United States Patent [19]

Karnosky

[11] Patent Number: Plant 6,983

[45] Date of Patent: Aug. 15, 1989

[54] CHINESE ELM CULTIVAR NAMED "AROSS/CENTRAL PARK"

[75] Inventor: David F. Karnosky, Chassell, Mich.

[73] Assignees: Central Park Conservatory; Arthur Ross Foundation, Inc., both of New York, N.Y.

[21] Appl. No.: 151,001

[22] Filed: Feb. 1, 1988

[51] Int. Cl.[4] ..... A01H 5/00

[52] U.S. Cl. ..... Plt./51

[58] Field of Search ..... Plt./51

[56] References Cited

PUBLICATIONS

'Aross Central Park' Chinese Elm, Karnosky, Hort. Science, 23(5):925–926, 1988.

Standard Cyclopedia of Horticulture, Bailey, 1935, McMillan Co., p. 3413, cited.

Trees, Shrubs, and Vines, Viertel, 1959, Syracuse Univ.

Manual of Cultivated Trees and Shrubs, Rehder, 1960, McMillan Co., pp. 181–182, cited.

Trees for American Gardens, Wyman, 1965, McMillan Co., p. 470 cited.

*Primary Examiner*—Robert E. Bagwill

*Attorney, Agent, or Firm*—Michael, Best & Friedrich

[57] ABSTRACT

A new and distinct variety of elm tree which produces leaves which are somewhat larger than other Chinese Elm cultivars with which it is most closely similar and which further exhibits cold hardiness to Zone 6 under typical environmental conditions.

1 Drawing Sheet

BACKGROUND OF THE NEW VARIETY

The present invention relates to a new and distinct variety of Chinese Elm Cultivar which has been denominated varietally as "ARoss/Central Park" and more particularly to such a Chinese Elm Cultivar which is somewhat similar in its overall botanical characteristics to the "Dynasty"; "Supervirens"; and "Drake"; Chinese Elm Trees but which is distinguished therefrom, and characterized principally as to novelty by being larger in size at full maturity as compared with the other varieties of Chinese Elm trees which it is most closely similar to, and by further producing leaves which have larger physical dimensions, the new and novel variety of Chinese Elm tree displaying noteworthy cold hardiness and disease resistance.

The Chinese Elm Tree *Ulmus parvifolia* is generally considered to be an attractive medium-sized ornamental tree which has excellent urban-hardiness and pest resistance. Introduced into cultivation in the late 1700's, this particular species of tree commonly is utilized in parks, on lawns, and in street-side locations. Heretofore it has been generally well-accepted that the use of most varieties of Chinese Elm Trees was probably limited to the southern portion of the United States including California, by reason of the variety's inability to withstand the extreme cold temperature experienced in the northern part of the United States. For example, the Chinese Elm Cultivars utilized frequency in this country, that is, "Dynasty" "Supervirens", "Drake" and "Tree Green" are most often cultivated in the southern states. In light of the noteworthy characteristics of the Chinese Elm Tree, nurserymen have long expressed a desire to locate a Chinese Elm Tree which would have an increased level of cold hardiness thereby permitting the species to be utilized in cited in the northern half of the United States. In this regard, it has been determined that the new variety of Chinese Elm Cultivar "ARoss/Central Park" is cold hardy to Zone 6 [Arnold Arboretum Hardiness Zones] and will readily grow in protected areas of Zone 5. Thus, the subject variety is one of only a very few cold hardy Chinese Elm Cultivars known at the present time.

ORIGIN AND ASEXUAL REPRODUCTION OF THE NEW VARIETY

The present variety of Chinese Elm Tree "ARoss/-Central Park" was discovered by the inventor in a cultivated area within the boundaries of Central Park, New York City, in 1976. The inventor, at that time, noted the novel characteristics of the tree and marked it for subsequent observation. The new variety of Chinese Elm Tree is of unknown parentage and the inventor has discovered through the conduct of research that it was planted over 100 years ago. More particularly, the third annual report of the Board of Commissioners for the New York City Department of Public Parks lists the same tree as being in its present location [near Fifth Avenue and 72nd Street] in 1873. The newly discovered tree is now over 60 feet tall and has a diameter at breadth height [DBH] of approximately 45 inches. The inventor believes that this represents the largest specimen of Chinese Elm presently growing in this country.

The first asexual reproduction of the newly discovered Elm Cultivar took place in 1976 when the inventor removed softwood cuttings of the subject tree, rooted them, and thereafter evaluated the progeny produced from this procedure. Subsequent evaluations have indicated that the progeny produced from this technique have the same distinctive characteristics as the newly discovered tree. The inventor has repeatedly vegetatively propagated the trees in the years since 1976, and has experimentally examined it during the past 10 years in confidential cooperation with city arborists and nurseymen in various parts of the country to determine its growth and survival characteristics.

BRIEF DESCRIPTION OF THE DRAWINGS

The accompanying drawing includes a color photograph of a characteristic twig bearing typical leaves; a photograph of the mature parent tree as it grows in Central Park in New York City; and a photograph of an immature tree during mid-season; all of the subject variety.

DETAILED DESCRIPTION

Referring more specifically the botanical details of this new and distinct variety of Chinese Elm Tree, the following has been observed under the ecological conditions prevailing at the inventor's facilities near Houghton, Mich. All major color code designations are by reference to the Inter-Society Color Council, National Bureau of Standards and The Horticultural Colour Chart (Wilson-1983). Common color names are also employed occasionally.

TREE

Generally: The "ARoss/Central Park" Chinese Elm Tree is considered to be a moderately fast-growing, urban-hardy tree. The original parent tree has thrived for over 100 years in New York City.

*Immature plants — Size.*—Seven, (7) year old rooted cuttings of this new Chinese Elm cultivar have an average height of approximately 18 feet [5.48 meters].

*Immature plants — Trunk.*—Seven, (7) year old rooted cuttings have a trunk thickness of approximately 4.5 inches [113.7 millimeters] DBH, and a 15 foot [4.56 meter] crown spread.

*Bark — Color.*—Young trees display a grey color, [110. gy. O1]. Further, new growth which is less than one year old has a yellow-green color [116. brill. Y G].

*Surface texture — immature growth.*—Smooth.

*Bark — mature trees.*—Light grey [110. gy. O1], occasionally light brown, although this color is not particularly distinctive of the subject variety.

*Surface texture — Mature growth.*—Fissured into irregular plates.

*Underbark.*—Color — the variety displays a light brown underbark, [72. d. O Y].

*Height.*—Mature plants — large as compared with other varieties which it is most closely similar to. The original parent tree is approximately 60 feet tall (18.28 meters).

*Trunk.*—Thickness — a mature specimen of the new variety of Chinese Elm Tree which is approximately 100 years old has achieved a diametral thickness of approximately 45 inches [1.14 meters] DBH.

*Lenticels.*—Color — yellowish-brown [71. m. O Y]. Numbers — approximately 19 lenticels per square inch are found on immature branches. Size — approximately 0.8 millimeters.

Leaves:

*Size.*—Generally — large as compared with other Chinese Elm Cultivars.

*Length.*—Mature leaves — variable, approximately 5.6 through 8.6 centimeters.

*Width.*—Mature leaves — variable, approximately 2.6 through 4.5 centimeters.

*Color — Generally.*—The top surface of immature leaves display a light green color [100. deep g y.]

*Surface texture — Immature growth.*—Soft and thin.

*Color — Mature leaves.*—The top surface of mature leaves takes on a dark green color [125. m. O1 G]. The bottom surface of mature leaves takes on a light grey-green color, [120. m Y G].

*Color — Fall.*—The top surface is mimosa yellow (Wilson 602).

*Surface texture — Generally.*—Lustrous in appearance and becoming increasingly thick and leathery with advancing senescence. Glabrous.

*Leaf shape.*—Generally — elliptical and occasionally ovate with a slightly oblique or inequilateral base.

*Leaf base-shape.*—Cuneate and forming an approximate 45 degree angle.

*Marginal form.*—The leaf margin is characterized by single, somewhat rounded serrations. Further, the marginal edge is considered somewhat undulate.

*Leaf tip.*—Acute.

*Leaf arrangement.*—Alternate.

*Mid-vein.*—Generally — prominent. Thickness — approximately one millimeter. Color — variable, [89. p Y through 100 deep g. y], darkening with senescence, [87. m. Y].

*Petiol.*—Length — approximately 9 millimeters. Thickness — approximately 1.5 millimeters.

*Flowers.*—Generally — Flowering of the subject variety occurs in late summer, depending upon environmental conditions. As a general matter, seeds are generally ripe in October in the New York City area.

*Length.*—Generally — the seeds of the subject variety are approximately 5/16 inches long, [7.938 millimeters].

*Seeds.*—Shape — average for the subject variety.

*Samaras.*—Color — these appear red in color as the seed reaches its full mature size. The color is not particularly distinctive of the subject variety however.

*Branching.*—Generally — The branching habit is considered spreading, depending upon pruning practices, with strong, angular branches which generally fan out from a position where the crown originates. These branches are very strong and storm related stem or branch breakage is only rarely evident.

*Hardiness.*—Generally — the new and novel variety of Elm Tree hereof is well suited for growing in hardiness Zones 6 and above. The inventor has heretofore grown the new variety in hardiness Zone 5 where it survives but it occasionally suffers winter branch and twig dieback. Moreover, the inventor has grown the new variety in Northern Michigan, which is considered Zone 4, where it will survive, but only in protected areas. This tree could be utilized widely in the geographical areas located immediately south of New York City with no worry of winter damage. Branch and twig dieback has occurred when winter temperatures have reached minus twenty degrees Fahrenheit and significant mortality of young trees has occurred when temperatures have reached minus twenty-six degrees Fahrenheit.

*Culture: Generally — the "ARoss/Central Park" Chinese Elm Tree roots easily from softwood cuttings. More particularly, three to five inch long cuttings* [76.2 through 127 millimeters] are dipped in Hormodin 2 and placed in a one to one mix of peat and perlite under intermittent mist. Under these conditions cuttings root with high frequency in approximately one month. Further, rooted cuttings grow well in a one to one mix of peat and potting soil. Plants can be expected to reach a height of two to four feet, [0.610 through 1.2 meters] in approximately two growing seasons.

The new variety of elm tree hereof is tolerant of a wide range of soil types and has been noted to thrive in soils ranging from compacted clay soils characteristic of Central Park, New York City, to a highly porus landfill, and sandy and gravelly soils. Controlling competing vegetation and irrigation will increase the growth rate, it being previously determined that the average growth rate under nursery conditions can be expected to average approximately 22 to 25 inches [approximately 0.61 meters] per year. It has been noted that young trees have a tendency to head early in the nursery bed and will need pruning to develop the crown at a suitable height above the ground.

The inventor has propagated approximately one thousand experimental trees by rooting of cuttings from the parent tree. These experimental trees are being grown at various test nurserys and by the New York City Parks Department for use in city parks.

Although the new variety of elm tree possesses the described characteristics as a result of the growing conditions prevailing in New York City, it is to be understood that variations of the usual magnitude and characteristics incident to growing conditions, fertilization, pruning and pest control are to be expected.

Having described and illustrated my new variety of elm tree, what is new and desired to be secured by plant letters patent is:

1. A new and distinct variety of Chinese Elm tree, substantially as illustrated and described, and which is somewhat remotely similar to the "Dynasty", "Supervirens", and "Drake" varieties of Chinese Elm tree with which it is remotely related, but which is distinguished therefrom and characterized principally as to novelty by being increasingly cold hardy and growing taller than other Chinese Elm Cultivars. While retaining the urban hardiness characteristics of and by producing larger leaves than that typically displayed by other Chinese Elm trees with which it is most closely similar, the new and novel variety of Chinese Elm having noteworthy height characteristics under typical Zone 6 conditions.

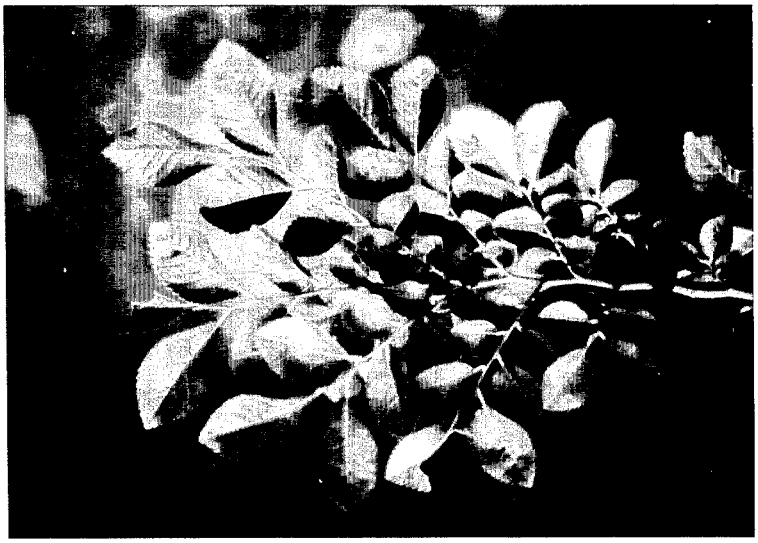
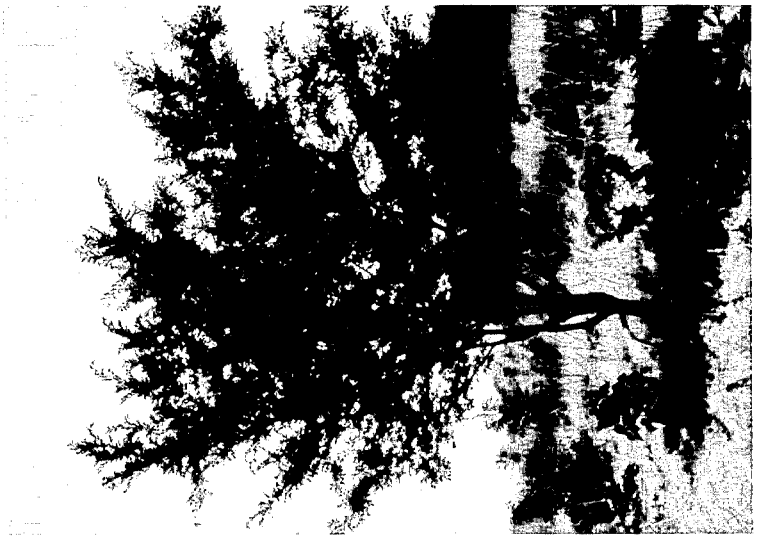
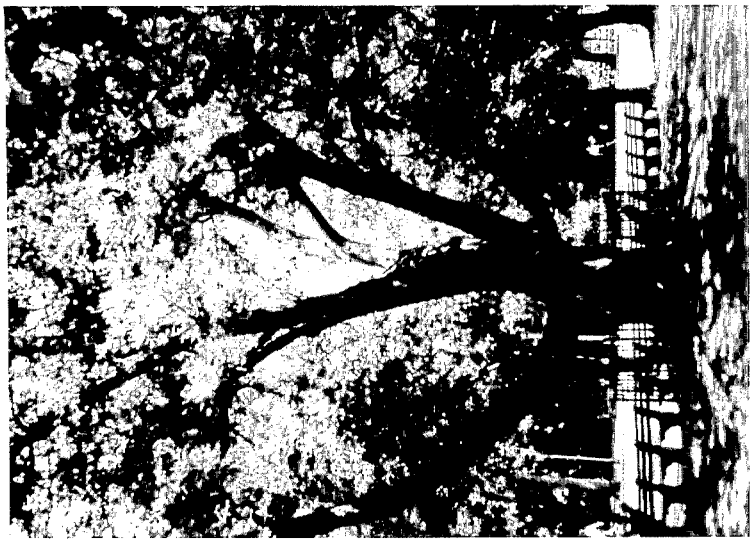

* * * * *